United States Patent [19]
Jantsch et al.

[11] Patent Number: 4,839,588
[45] Date of Patent: Jun. 13, 1989

[54] METHOD FOR THE EXAMINATION OF ELECTRICALLY ACTIVE IMPURITIES OF SEMICONDUCTOR MATERIALS OR STRUCTURES AND MEASURING ARRANGEMENT FOR CARRYING OUT THE METHOD

[75] Inventors: Wolfgang Jantsch, Linz, Austria; György Ferenczi, Budapest, Hungary

[73] Assignee: Magyar Tudomanyos Akademia Muszaki Fizikai Kutato Intezet, Hungary

[21] Appl. No.: 138,195

[22] PCT Filed: Mar. 17, 1987

[86] PCT No.: PCT/HU87/00016
§ 371 Date: Nov. 25, 1987
§ 102(e) Date: Nov. 25, 1987

[87] PCT Pub. No.: WO87/05701
PCT Pub. Date: Sep. 24, 1987

[30] Foreign Application Priority Data
Mar. 17, 1986 [HU] Hungary ............................. 1096/86

[51] Int. Cl.$^4$ ............................................. G01R 31/26
[52] U.S. Cl. ............................ 324/158 D; 324/158 R; 324/158 P; 324/58 B
[58] Field of Search ............ 324/73 R, 73 PC, 158 R, 324/158 T, 158 D, 95, 58 B, 58 R, 158 P

[56] References Cited
U.S. PATENT DOCUMENTS

| | | | |
|---|---|---|---|
| 4,169,244 | 9/1979 | Plows | 324/158 R |
| 4,563,642 | 1/1986 | Munakata | 324/158 R |
| 4,686,463 | 8/1987 | Logan | 324/158 P |
| 4,704,576 | 11/1987 | Tributsch | 324/158 R |
| 4,727,319 | 2/1988 | Shahriary | 324/158 P |

Primary Examiner—Michael J. Tokar
Attorney, Agent, or Firm—Handal & Morofsky

[57] ABSTRACT

A method for the examination of electrically active impurities of semiconductor materials or semiconductor structures is disclosed. The method comprises the steps of providing a junction in a sample taken from the semiconductor to be tested, inserting the sample in a microwave field, providing a space charge layer in the junction by applying a reverse bias thereto, filling the electrically active defects of the space charge layer, and examining the thermal emission process proceeding to reach a thermal equilibrium state that occurs following the filling step by measuring the change of the microwave field that takes place due to changes in microwave absorption in the sample during the thermal emission process. The microwave field should be present at least during the examination of the transient microwave absorption. In a measuring arrangement for carrying out the method a sample (24) of the semiconductor comprises a junction, the sample is provided with a pair of electrical contacts, and the measuring arrangement comprises a biasing means (26) coupled to the contacts for reverse biasing the junction to provide a space charge layer therein, a means (26) for filling the electrically active defects in the layer during a predetermined period or periods, and transient detecting means (27) for detecting transient changes in the junction after termination of said periods. The arrangement further comprises a microwave generator (21), a microwave means (23) coupled to the generator which defines a microwave field, and the sample is arranged in the field of the microwave means with a contact coupled to ground. The transient detecting means (27) is a microwave detector arranged to detect transient changes in microwave absorption due to the changes in the junction.

18 Claims, 4 Drawing Sheets

METHOD FOR THE EXAMINATION OF ELECTRICALLY ACTIVE IMPURITIES OF SEMICONDUCTOR MATERIALS OR STRUCTURES AND MEASURING ARRANGEMENT FOR CARRYING OUT THE METHOD

FIELD OF THE INVENTION

The invention relates to a method for the examination of electrically active impurities (deep levels) of semiconductor materials and to a measuring arrangement for carrying out the method.

BACKGROUND OF THE INVENTION

Electrically active impurities such as foreign atoms, native defects of the crystal or the complexes thereof can all exert a significant influence on the electrical and optical properties of semiconductor materials as well as of structures and devices made of such materials, therefore the examination of such impurities forms an indispensable method both of the research of semiconductor materials and of the quality control of manufacturing processes of active elements in the field of microelectronics.

For investigating semiconductor materials and controlling active elements the sensitivity limit for detecting electrically active impurities should be at least $10^{10}$ atoms/cm$^3$. At present such a high sensitivity can be obtained by measuring a particular single process only. In such a process a space charge layer is provided in the semiconductor under test which can be realized by depositing a suitable metal layer (i.e. forming a Schottky diode), by forming a p-n junction or by establishing a MOS structure, etc. In case of a reverse bias the space charge layer has insulating properties i.e. it does not comprise free carriers. Those portion of electrically active defects which fall within the space charge layer can be either in an electrically active or neutral state. In the process in question the active defects are filled with free charge carriers and the subsequent thermal emission recovery process is examined.

In a known examination method of this process the structure is electrically short-circuited and cooled down from room temperature to the temperature of liquid nitrogen, and in this latter temperature a reverse bias is applied to the sample. The electrically active defects remain saturated with free charge carriers that correspond to a non-equilibrum thermal state. The time constant of the recovery process to the thermal equilibrum is $$\tau_n^{-1} = e_n = N_c \sigma v \exp(-E_T/kT) \qquad (1)$$

wherein
- $\tau_n$ is the time constant of the thermal emission process
- $e_n$ is the probability of the thermal emission
- $N_c$ is the density of the state in the valence band
- $\sigma$ is the capture cross section
- $v$ is the thermal drift velocity
- $E_T$ is the activation energy of the electrically active defects in electronvolt units
- $k$ is the Boltzman constant
- $T$ is the temperature expressed in Kelvin.

In low temperature this time constant can be even some years long. It follows from equation (1) that the time constant decreases exponentially with increasing sample temperatures, and the thermal emission takes place when the characteristic temperature associated with the electrically active defects has been reached. The free charge carriers released during such emission can be detected by means of conventional current measurement or by detecting the changes of the capacitance of the sample. Corresponding known experimental methods are as follows:

Thermally Stimulated Current i.e. TSC is described e.g. by R. H. Bube: 'Photoelectronic Materials and Devices' Ed. S. Larach pp. 100–139, 1965 (D. Van Nostard Comp.).

Thermally Stimulated Capacitance, i.e. TSCap is described e.g. by Carabelles at al: Solid-St Communication 6, 167, 1968).

Another widely used way of examining the thermal emission process is represented by the transient measurement technique. In such technique the sample under test is reverse biased at predetermined constant temperature and short circuited during perodically repeated short intervals. During the short-circuiting intervals the defects are filled with free charge carriers and during re-establishment of the reverse bias a thermal emission recovery process is started which has the characteristic time constant defined by the equation (1).

The filling of defects can be made not only in an electrical way by short-circuiting the sample but also by optical excitation, by an electron beam or by means of other kinds of ionizing radiation. The excitation should be, however, periodically repetitive.

The thermal emission can be detected from the transient changes in the capacitance or current of the sample under test, see e.g. R. Williams, J. Appl. Phys. 37, 3411 (1966).

The automatic detection and evaluation of the transients have been solved by means of Deep Level Transient Spectroscopy (DLTS) technique. Such a method is described e.g. by Miller et. al: Rev. os Sci. Instrum 48, pp. 237–239, 1977 or in Hungarian Pat. No. 181.136. Owing to the possibility of their automated performance DLTS measurements have become the most widely used methods of examining thermical emission processes.

The use of DLTS technique is connected with a number of factors influencing or limiting the sensitivity, accuracy and conditions of the measurements. In the following discussion these limiting factors will be analysed in a more detailed way because the understanding of these facts is thought to be inevitable for the correct evaluation of the prior art.

In the methods based on transient capacitance measurements the capacitance represented by the sample under test is connected in a measuring bridge and excited by a high frequency signal. The examined transient capacitance is represented by a component of the high frequency output signal of the bridge which has a predetermined phase. The first limit of such measurements is formed by the upper limit of the applicable frequency. Owing to the serial resistance of the sample which is higher than zero, the following equation exists between the measured and actual capacitance of the sample:

$$C_m = (C_i/1 + (\omega C_i R_i)^2) \qquad (2)$$

in which
- $C_m$ is the capacitance value detected by the capacitance meter
- $C_i$ is the actual capacitance of the sample $R_i$ is the serial resistance of the sample $\omega$ is the frequency of the capacitance measurement.

In everyday practice there are samples which have serial resistances higher than 100 ohms and the capacitance of such samples cannot be measured if the measuring frequency is higher than about 1 MHz. For that reason the operational frequency of the capacitance bridge in commercially used instruments is not higher than 1 MHz. In the practice, however, there exists a number of semiconductor samples with serial ohmic resistances much higher than 100 ohm and one can even meet as high resistance values as 1 Mohm. Such samples cannot be measured by DLTS methods or if still measured in that way, the sensitivity of the measurement will drop well below the required level.

In addition to the limitations caused by the presence of the series resistance the shunting effects of the leakage currents flowing in the samples represent a further limitation by decreasing the sensitivity. Owing to non-ideal surface of the semiconductor samples a certain amount of leakage current is always present when being reverse biased. If as high sensitivity is requested as mentioned hereinabove then the maximum permitted leakage current should be about 1 $\mu$A. This condition cannot be satisfied easily therefore it represents a further limitation regarding the types of samples that can be examined and/or the maximum sensitivity.

Of these reasons the maximum of the measuring frequency cannot be higher than about 1 MHz which, however, limits the maximum frequency of the control pulses which alternatively excite and reverse bias the sample. In case of a measuring frequency of 1 MHz, the response time of the capacitance meter is at least 5 $\mu$s long and the actual measurement cannot start before the treble of the response time has elapsed. Even if the duration of the measurement periods is chosen to be just as short as the combined duration of the exciting pulses and the subsequent dead periods, the maximum of the repetition frequency cannot be higher than about 25 kHz. This theoretical upper limit is substantially higher than the highest one of the repetition frequencies used in the practice (see Hungarian Pat. No. 182.777).

It is well known in the art that DLTS measurements are carried out generally when the temperature is varied. The changing of the temperature is disadvantageous because in addition to the comparatively long time of measurements (which can be typically between 20 minutes and two hours) it can result in the thermal treatment of the sample under test and can rearrange the structure of the defects. According to the DLTS measurement with constant phase position lock-in amplifier as disclosed e.g. in Hungarian Pat. No. 181.136 frequency-scan DLTS measurements with constant temperature can be carried out, however, the attainable frequency range is limited by the maximum frequency of capacitance measurement which is about 25 kHz and of practical considerations the lowest frequency cannot fall below 0.25 Hz. With such upper and lower limits the frequency range cannot exceed more than 5 decimal orders of magnitude.

In the paper of G. Ferenczi: 'The Examination of electrically active impurities of semiconductor materials and structures' (Hiradastechnika XXXVI. 1985. 10. pp. 451–454) the frequency scan DLTS measurement is described which can offer a deep level spectrum that has an extreme value proportional with the emission time constant characteristic to the type of the particular impurity. With the attainable maximum frequency coverage of $10^4$–$10^5$ and in case of a given temperature, it is possible to detect deep levels falling in the range of activation energies between E=0.2–0.3 eV. Of that reason the practically significant range of activation energies between 0.05 eV to 0.7 eV can be covered by the frequency scan method if the measurements are repeatedly carried out in different temperatures. The corresponding temperature range is typically between 240K. and 330K. For enhancing the range of frequency scan measurements in a predetermined single temperature to cover the energies of 0.05 to 0.7 eV it is required that the frequency coverage be as high as $10^{11}$. Due to the practical limitations explained above such a wide range was not realizable. Of that reasons the examination of the full deep level spectrum inevitably required the changing of the measuring temperature that was connected with the drawbacks associated with the unwanted thermal treatment (annealing) of the sample.

A further limiting feature lies in the relative character of the sensitivity of capacitance DLTS measurements. It is a well known fact that in such measurements:

$$\frac{N_T}{2N_D} \simeq \frac{\Delta C}{C_o} \tag{2}$$

in which $N_T$ is the deep level concentration $N_D$ is the shallow level dopant concentration $\Delta C$ is the capacitance change $C_o$ is the capacitance of the sample.

The lowest practically measureable capacitance change is about $2 \times 10^{-5}$ pF (see e.g. the Hungarian Pat. No. 182.777). Taking this fact into consideration the maximum attainable sensitivity is $$\text{minimum of } (N_T/N_D) = 2 \cdot 10^{-6} \tag{4}$$

In case of typical concentration of dopants, this sensitivity represents a detection limit level of $10^{10}$ atoms/cm$^3$. One should, however, bear in mind that in case of higher concentration of dopants the detection limit decreases, thus in such samples the required sensitivity cannot be reached.

The above referred paper of G. Ferenczi refers also to the fact that in DLTS measurements the capture cross section can be determined by changing the width of the exciting pulses. The accuracy of such a measurement is limited by the minimum width of the exciting pulses which is about 1–2 ns and with such data higher capture cross section than $\sigma = 10^{-15}$ cm$^2$ cannot be measured, however, the largest value which should be measured is $\sigma = 10^{-12}$ cm$^2$.

This limit can be derived from the fact that in case of a capacitance measurement the sample under test should be arranged in the bridge in an isolated way i.e. unearthed. Since the measurements are carried out under varying temperatures, the practically realizable measuring arrangements are using at least 30 cm long connecting cables. With such cable lengths one cannot apply shorter exciting pulses than 1–2 ns.

Summarizing the above thoughts it can be stated that the practically attainable best parameters of capacitance DLTS measurements are as follows:

the maximum sensitivity $N_T/N_D \geq 10^{-6}$ which corresponds to a detecting limit of $N_T \geq 10^{10}$ atoms/cm$^3$, the maximum coverage range of the repetition frequency of the exciting pulses is about $10^5$, the minimum width of the exciting pulses is 1-2 ns,
the highest tolerable leakage current is 1 μA (in case of maximum sensitivity),
the highest measuring frequency is 1 MHz,
the highest series resistance of the sample is about 100 ohm.

It is known in the art that very small changes of microwave absorption can be measured with a high accuracy e.g. in a microwave cavity. Such measurements are used e.g. for the examination of the paramagnetic resonance of electrons (see e.g.: G. Feher, Bell System Technical Journal 36, pp. 444–484, 1957). By means of microwave absorption measurements transient phenomena can also be detected. The measurement of lifetime of minority charge carriers by changing the microwave absorption as a function of time has been described first by Jacob et al. in the Proceedings of the IRE 48, pp. 229–233, 1960. During the lifetime measurements of minority charge carriers the change in microwave absorption due to the presence of non-equlibrum free charge carriers is detected. This method has become a widely used technique (e.g. R. I. Desi et al. Rev. Sci. Instrum. 55, pp. 1343–1347, 1984).

During lifetime measurements but also during other kinds of measurements based on microwave absorption the sample under test is not provided with contacts for electrical connections. Without electrical contacts the generated non-equilibrum carriers will move away with thermal drift velocity in the material sample and their number changes with the recombination process. The presence of free charge carriers in the sample is therefore determined by the recombination process. The above referred measurement technique, which aims at detecting the lifetime of minority carriers in the sample, is principally inappropriate for determining the time constant of thermal emission.

OBJECT OF THE INVENTION

The object of the invention is to provide a method and a measuring arrangement for the examination of electrically active impurities of semiconductor materials and structures, in which the detection of the thermal emission process is based on an effect which is basically different from those of the aforementioned conventional methods and in which the factors limiting the performance of the measurements are much less significant.

SUMMARY OF THE INVENTION

The method according to the present invention is based directly on the recognition according to which microwave absorption technique can be used for detecting and measuring the thermal emission of charged electrically active impurities of a sample under test which emission takes place when a space charge has been established, such a use requires, however, that electrical connections be made to the semiconductor junction forming the sample to provide the electrical voltage that establishes the space charge and to periodically fill the completely or partially depleted deep levels. By chosing an appropriate measuring arrangement the presence of the electrical connections to the sample cannot affect the microwave field significantly in the test region i.e. in a microwave cavity or waveguide.

According to the invention a method has been made for the examination of electrically active impurities of semiconductor materials or semiconductor structures which comprises the steps of providing a junction in a sample taken from the semiconductor to be tested, inserting the sample in a microwave field, providing a space charge layer in the junction by applying a reverse bias thereto, filling the electrically active defects of the space charge layer, examining the thermal emission process aiming at reaching a thermal equilibrum state that takes place following said filling step by measuring the change of the microwave field that takes place due to changes in the microwave absorption in the sample during the thermal emission process. The microwave field should be present at least during the examination of the transient of the microwave absorption.

The filling of the defects can be made by a single shot, however, it is often preferable if this step and the subsequent examination are periodically repeated.

In that case the repetition frequency can be changed to cover a range of at least 6 decimal orders of magnitude and/or the duration of the filling pulses is changed and the transient response can be examined in case if the filling pulses are shorter than 1 ns.

By changing the repetition frequency and/or the wdith of the filing pulses pure frequency scan measurements can be made which can be carried out at a single temperature.

It is most convenient if the filling of the deep levels is provided by the application of an electrical exciting pulse lead to the sample which decreases or eliminates the space charge region.

Instead of such an electrical pulse the deep levels can be filled also by light, by an electron beam or by means of an other kind of radiation.

In case of certain kinds of examinations it can be preferable if the measurements are carried out at different constant temperatures or if the temperature of the sample is continuously changed.

The semiconductor to be tested may comprise already a junction, however, if this is not the case the junction required for the measurements can be provided by forming a Schottky barrier, a MOS capacitor or a p-n junction in the sample.

It is preferable if the sample is exposed to the microwave field in a microwave resonator or in a microwave reflectometer.

The transient measurements can be facilitated if the microwave field is substantially eliminated during the filling step. This can be achieved not only by switching off the microwave field for the time of the filling pulses but also by de-tuning the microwave frequency to an extent which cannot disturb (overdrive) the sensitive microwave detection.

According to the invention a measuring arrangement has also been provided for the examination of electrically active impurities of semiconductor materials or semiconductor structures, in which a sample of the semiconductor comprises a junction, the sample is provided with a pair of electrical contacts, and the measuring arrangement comprises a biasing means coupled to the contacts for reverse biasing the junction to provide a space charge layer therein, a means for filling the electrically active defects in the layer during a peredetermined period or periods, and transient detecting means for detecting transient changes in the junction after termination of said periods, and the arrangement comprises furthermore a microwave generator, a microwave means coupled to the generator which defines a microwave field, and the sample is arranged in the field of the microwave means with a contact coupled to earth, the transient detecting means is a microwave detector arranged to detect transient changes in the microwave absorption due to the changes in the junction.

In a preferable embodiment the biasing and filling means are implemented by a pulse generator that establishes periodical filling pulses and provides a reverse bias to the junction during intervals of the pulses.

In a further preferable embodiment a transmission line connects the pulse generator in the sample.

In another preferable embodiment the microwave means is a cavity resonator and the sample is arranged in the resonator at the maximum of the electrical field.

In an alternative embodiment the microwave means is a microwave reflectometer.

It is also preferable if the temperature of the sample can be changed and to this end the arrangement comprises a temperature controlling means in which the sample and the microwave means can be arranged.

DESCRIPTION OF THE DRAWINGS

The invention will now be described in connection with preferable embodiments thereof, in which reference will be made to the accompanying drawings. In the drawing.

DETAILED DESCRIPTION OF THE PREFERABLE EMBODIMENTS

Figure 1:
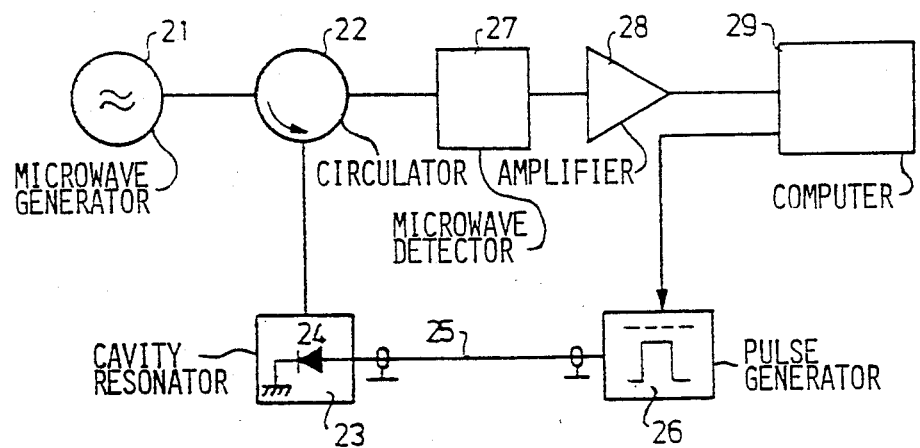
FIG. 1 is a general schematic diagram of a first embodiment of the measuring arrangement according to the invention.

For using the method according to the invention an experimental setup is required which allows the time-resolved detection of the microwave absorption of a Schottky diode or a p-n junction or a MOS structure, etc. with a maximum sensitivity. FIG. 1 shows schematically an arrangement usable for such measurements.

A frequency and amplitude stabilized microwave generator 21 (which can be a Klystron, Gunn oscillator, IMPATT diode, FET oscillator, etc.) is connected to first port of circulator 22. A next allowed exit port of the circulator 22 leads to microwave resonator 23 in which sample 24 is arranged, preferably in a maximum of the electrical field. The sample 24 is made of the material of investigation, within which the space charge region can be established. The sample 24 has two electrical connections, one of them is earthed and the other one is connected to pulse-transfer line 25 including an impedance matching network. Transfer line 25 and wiring within the resonator 23 should be arranged in such a way that the quality factor of the cavity formed by the resonator 23 is not impaired. In a cavity type resonator this requirement can be achieved by placing wires or coaxial cables along a "knot" line, where the electric microwave field vanishes.

By adjusting the microwave frequency and the coupling of the resonator 23, the microwave reflected by the resonator 23 (including the sample 24 and a portion of the transfer time 25) is minimized. This procedure is often referred to as 'critical tuning'. The reflectivity itself is measured by means of microwave detector 27 coupled to the next port of the circulator 22. The microwave detector 27 can be any suitable type, e.g. a crystal rectifier, a microwave Schottky diode with fast response time, etc. For a critically tuned resonator, any change in absorption causes a finite reflectivity, which is proportional in magnitude to the change in absorption.

The detected signals of the microwave detector 27 are amplified by selective amplifier 28, and the amplified signals are evaluated by computer 29 programmed to carry out such measurements. Computer 29 is capable of controlling the operation of pulse generator 26 that transmits via the transfer line 25 the dc bias pulses to the sample 24.

The emission of carriers from deep levels, which forms the phenomenon to be investigated by the present invention, is triggered periodically by first filling these deep levels by the application of a short electric pulse, which reduces the width of the space charge layer by reducing the reverse bias in the sample 24. By this filling pulse free carriers are swept into the space charge layer and a fraction of time is captured by deep level states. After the end of this filling pulse these captured charge carriers are emitted again with an emission rate which is characteristic to the trap under investigation. Both capture and emission change the number of free carriers in the sample and hence the microwave losses, i.e. the absorption. In the measuring arrangement shown in FIG. 1 the microwave absorption is obtained from the detector 27 as a function of time.

In order to determine the emission rate, which is the inverse of the time constant for the recovery of the microwave reflectivity following the filling pulse, the selective amplifier 28 is designed to selectively amplify the detected signal with respect to unavoidable background noises, whereby increased sensitivity can be reached.

Since a leadout contact of the sample 24 is earthed, both proper impedance matching and short transmission lines can be realized, and such an arrangement allows the application of narrow exciting pulses which can be as short as 100 ps.

Figure 2:
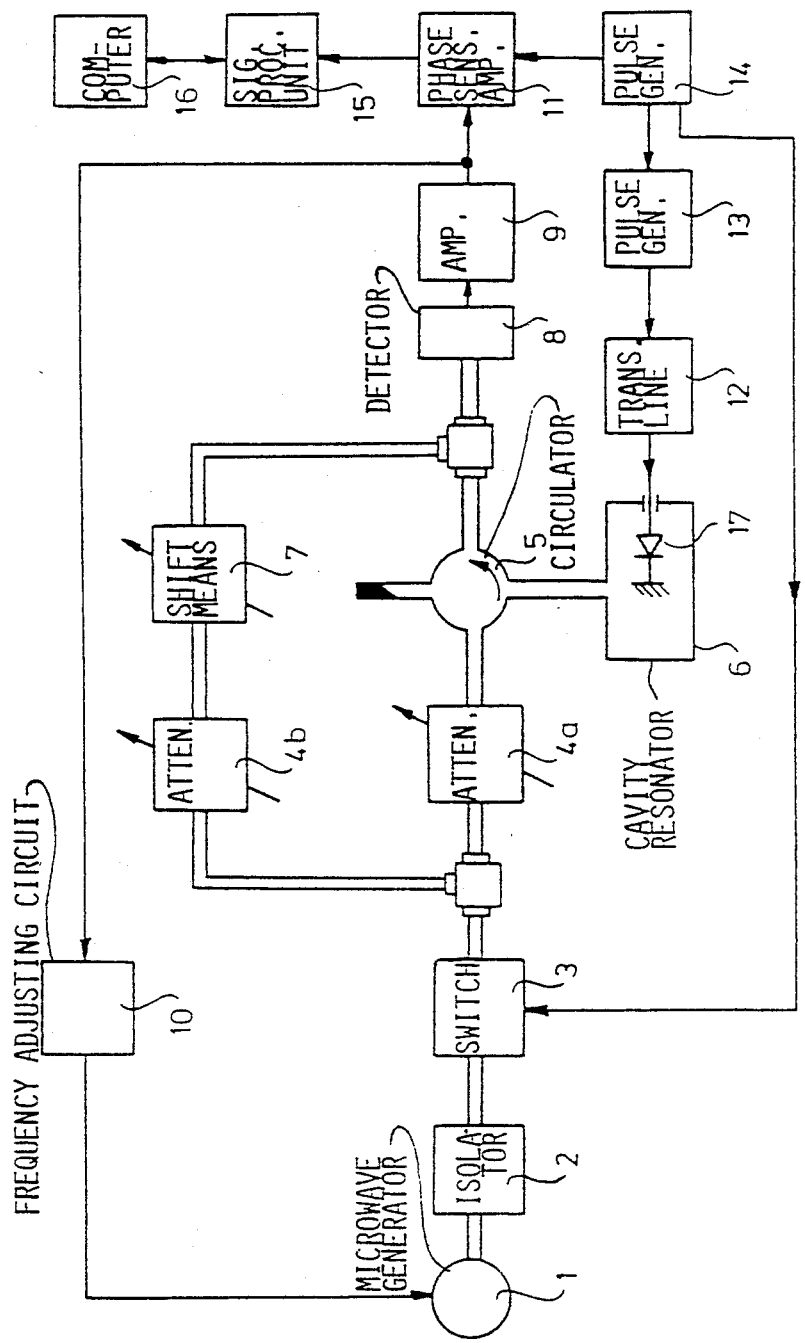
FIG. 2 is the block diagram of a further embodiment of the arrangement using a microwave bridge.

A further arrangement for measuring the microwave absorption is shown in FIG. 2, which uses a microwave bridge. The microwave circuitry comprises stabilized microwave generator 1, isolator 2 coupled to the output of the generator 1, a controlled switch 3 for disconnecting the passage of microwave signals in response to control pulses applied to its control input and a microwave bridge coupled to the output of the switch 3. A first branch of the bridge comprises a first attenuator 4a with adjustable attenuation, a circulator 5 with a first port connected to the output of the first attenuator 4a, a cavity resonator 6 connected to a further port of the circulator 5 and the end of the first branch is coupled to a third port of the circulator 5. The second branch of the bridge comprises a second attenuator 4b with adjustable attenuation coupled also to the output of the switch 3, and an adjustable phase shifting means 7. The two ends of the two branches are commoned and connected to microwave detector 8. The output of detector 8 is coupled via amplifier 9 to input of a phase-sensitive amplifier 11. An automatic frequency adjusting circuit 10 is fed back from the output of the amplifier 9 to the generator 1, the operation of which can be switched off for the time of transient measurements not to interfere therewith or which should have a response time much longer than that of the measured transient.

The output of the phase-sensitive amplifier 11 is connected to a signal processing unit 15 which in turn is coupled to computer 16 that evaluates and processes data obtained from the measurements.

The phase-sensitive amplifier 11 comprises a synchronizing input coupled to output of a pulse generator 14 which latter has two further outputs coupled respectively to trigger input of a further pulse generator 13 and to the control input of the microwave switch 3. The output of the second pulse generator 13 is connected via transmission line 12 to sample 17 arranged in the cavity 6. The transmission line 12, the sample 17 and the cavity 6 can be similar to those shown in FIG. 1. It is worth mentioning that a connection of the sample 17 is earthed and the transmission line 12 is capable of passing dc bias to the sample from the generator 13. The transmission line has preferably a 50 ohm characteristic impedance.

The cavity 17 can be of any suitable type, e.g. one of the standard cavities produced by the company Bruker Analytische Mestechnik GmbH, Silberstreifen, Germany and its loaded quality factor should be between about 1000 and 10.000. Further requirements that can be imposed on the resonator 6 lie in the possibility of providing electrical connections to the sample therein, the possibility of irradiating the sample by means of light or any other kind of radiation and finally that it should be insertable in a temperature regulator.

The second pulse generator 13 can be any suitable type, such as type AVP-AV of the Canadian company AVTECH, Ottawa. This pulse generator can generate pulses superimposed on an adjustable dc level, thus it is appropriate for reverse biasing the diode junction forming the sample and periodically short-circuiting or forward biasing the same.

The microwave bridge can be realized by a number of commercially available types, and in the following example a standard bridge of the Bruker company was used with an operational frequency of 9.6 GHz. The microwave frequency can be chosen to any suitable value between about 1 and 100 GHz and this selection depends primarily on the type of the available bridge and on the requirements imposed on the measurements.

The duration of the shortest detectable transient signals is limited primarily by the loaded quality factor $Q_L$ of the resonator 6. The resonance bandwidth of the cavity resonator 6 can be defined as:

$$f = (\omega_o / 3Q_L). \tag{5}$$

wherein:

$\omega_o$ is the frequency of the microwave generator 1 and $Q_L$ is the loaded quality factor of the cavity resonator 6.

The multiplier 3 in the denominator of equation (5) comes from the definition of the signal drop from 90% to 10% as the bandwidth. With the above referred typical $Q_L$ values varying between about 1000 and 10.000, the own response time of a transient measurement will be $\tau_C = 1/\Delta f$ which is 5 ns or longer. A corresponding response time in transient capacitance measurements is 5 μs or longer, thus the microwave detection of thermal emission (with a frequency of about 10 GHz) increases the measurable range of shortest thermal emission transients by a factor of at least 1000 compared to conventional techniques.

The timing of the measuring arrangement is controlled by the first pulse generator 14. This generator 14 delivers timing signals for the second pulse generator 13 that applies the exciting pulses to the sample 17. Generator 14 controls the phase position of the phase-sensitive amplifier 11 which receives detected signals representing the changes of microwave absorption in time, amplifies these signals and provides the average of the amplified signals phase-locked to a predetermined phase position defined by the control pulses from the pulse generator 14. The microwave signals applied to the microwave bridge are switched off by means of switch 3 for the duration of the exciting pulses coupled to the sample, and the corresponding gating pulses are generated by means of the pulse generator 14 for the switch 3.

The processing of the averaged transient signals at the output of the phase-sensitive amplifier 11 can be made in a number of ways. According to a suitable embodiment the signal processing unit 15 can be a fast transient recorder capable of digitizing and averaging the input signals representing the transients of the microwave absorption. The computer 16 is used for evaluating the output data of the transient recorder.

Figure 3:
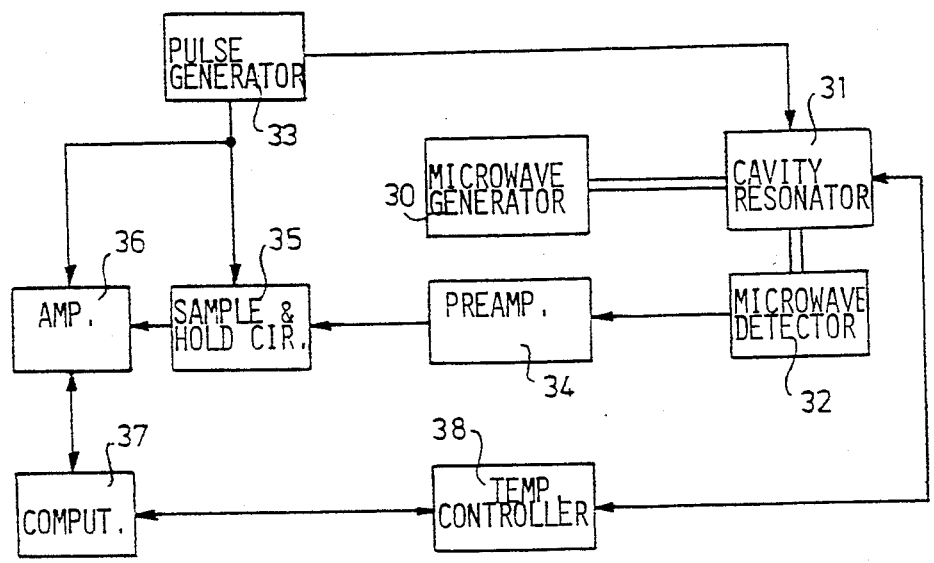
FIG. 3 shows a third embodiment of the arrangement.

A further embodiment of a measuring arrangement for detecting transients of microwave absorption is shown in FIG. 3. The arrangement comprises microwave generator 30 coupled to cavity 31 in which a sample (not shown) is arranged as in case of the previous embodiments. Microwave absorption in the cavity 31 is sensed by microwave detector 32, and the sample is controlled by pulse generator 33 just as in the case of the previous embodiments. Preamplifier 34 amplifies the detected signals to a suitable level, and sample and hold circuit 35 receives the samples. The output of the sample and hold circuit 35 is coupled to input of a lock-in amplifier 36 synchronized by output pulses of the pulse generator 33 in such a way that an averaging takes place which is in a predetermined phase-position relative to the exciting pulses applied to the sample. The pulse generator 33 controls the sample and hold operation, too. The output of the lock-in amplifier 36 is coupled to computer 37 for processing and evaluation. The temperature of the cavity 31 with the sample therein can be set and adjusted by means of temperature controller 38 reporting the actual temperature to the computer 37.

In an alternative embodiment the microwave cavity 31 can be replaced by a microwave reflectometer. The sample is arranged at an end portion of a waveguide excited by the generator 30 and a reflector of suitable size is placed behind the sample with a predetermined and adjustable spacing. The arrangement is adjusted in such a way that the reflected microwaves from the sample and from the reflector fully offset each other at the location of the detector 32. When the absorption changes in the sample, the compensation becomes less effective and the detector 32 detects the change in microwave level.

It is also preferable if the microwave level reaching the detector is substantially eliminated during the filling pulses. This can be achieved rather by de-tuning the generator 30 than physically disconnecting the microwave path. In that case the switch 3 in the FIG. 2 embodiment can be spared and an appropriate de-tuning signal should be applied to the generator. Obviously, the control of this function is identical with that of the switch 3.

The method according to the invention will now be illustrated by means of two examples.

EXAMPLE 1

The measuring arrangement shown in FIG. 2 was used. The microwave bridge was realized with an X band bridge of the aforementioned Bruker company operating at 9.6 GHz. The cavity resonator 6 was placed in a cryostat capable of circulating liquid helium made by the British company Oxford Instruments. The semiconductor sample 17 under test was placed on a cylindrical quarz rod with a diameter of 4 mm, and electrical contacts to the sample were made by means of respective gold wires of 20 μm diameter having lengths of 2 cm. This very short and thin connection was required for minimizing the load transformed in the cavity. Outside the cavity 6 the connection to the pulse generator 13 was made via a short coaxial cable of 50 ohms characteristic impedance. The resistance of the semiconductor sample was 10 ohmcm and the sample itself was an n type silicon crystal doped with phosphor. The crystal was heat treated in a nitrogen atmosphere at a temperature of 400° C., whereafter a wafer of 3 mm×2 mm×0.4 mm was cut from the crystal. A gold spot of 0.8 mm diameter was vacuum-deposited on a surface of the wafer and this gold layer formed the first electrode of a Schottky diode. The ohmic contact on the other side of the wafer was realized by building an indium alloy thereon. Under the effect of the heat treatment thermal donors were created in the sample with a concentration of $5.10^{14}$ atom/cm$^3$. During the measurement of thermal emission the $+/++$ transition of the filled thermal donors were detected by means of detecting the changes of microwave absorption.

The sample in the cavity 6 was measured in seven different constant temperatures in the temperature range between 55.5 K.° and 80.4 K.°. The sample was reverse biased by $-10$ V and it was periodically excited by pulses of 9 V amplitude and 20 μs width. The period time of the exciting pulses was continuously varied between 0.1 sec and $10^{-5}$ sec. The microwave power was switched off by means of switch 3 during the existence of the exciting pulses. The changes of the transient microwave absorption detected by the detector 8 was averaged by means of the signal processing unit 15. This operation was carried out by means of a lock-in amplifier controlled and synchronized as described in the Hungarian Pat. No. 182.777.

Figure 4:
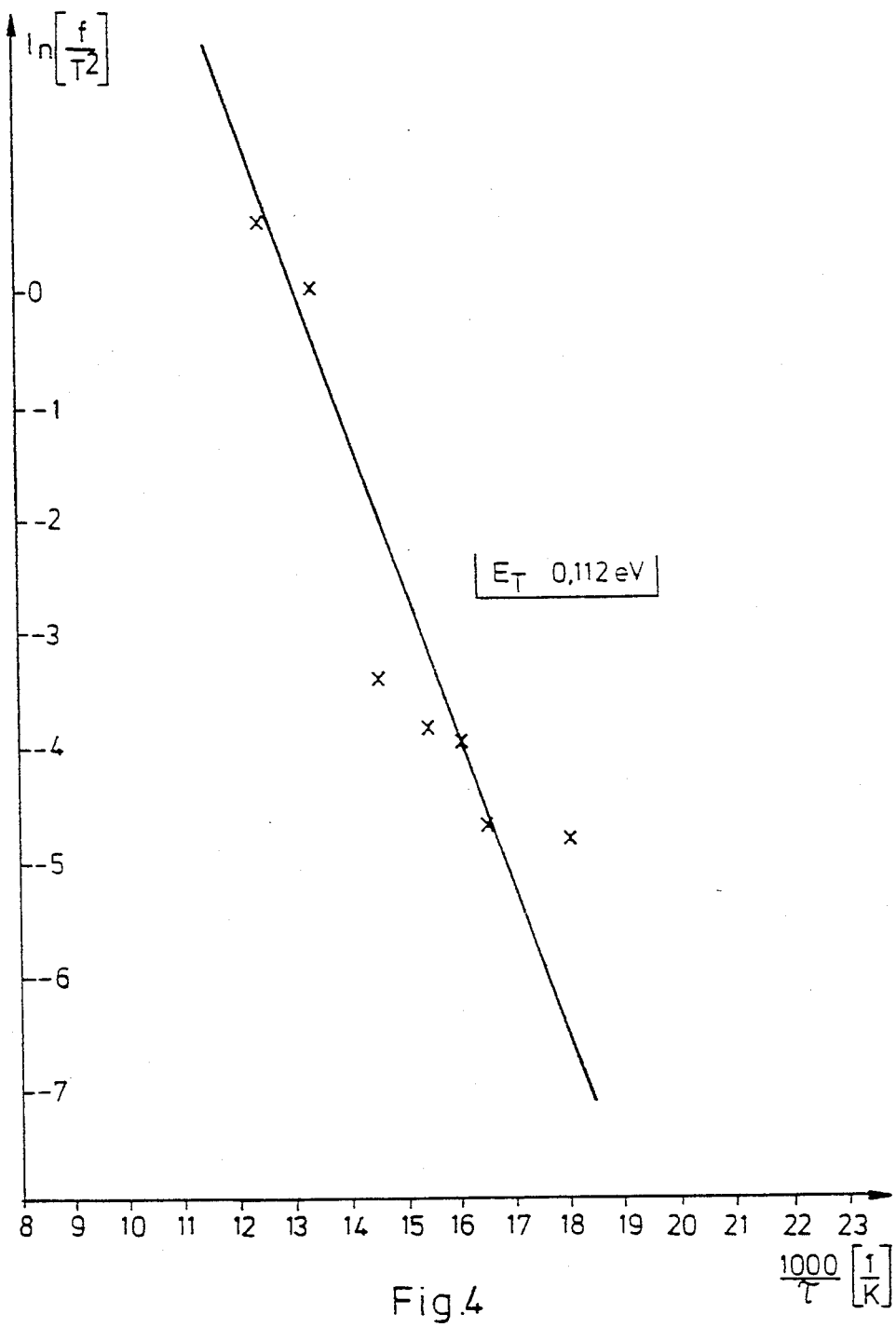
FIG. 4 shows the Arrhenius plot curve derived from the results of measurements made by the arrangment of FIG. 2.

The results of the measurements are illustrated in FIG. 4, in which the points indicated by x correspond to the frequencies associated with the signal maximums in the respective temperatures. The Figure is an Arrhenius plot of the temperature-dependency of the signal maximum as a function of frequency which is used for determining the activation energy of the deep level under test. The measured activation energy was $E_T=0.112$ eV which value fully coincides with the value measured by conventional DLTS technique for the $+/++$ transition of the thermal donor (see Kimerling et al. 'Appl. Phys. Letters 39 pp. 410-412, 1981').

EXAMPLE 2

The measuring arrangement of FIG. 3 was used to detect the microwave absorption transients of n-type FZ Si wafers with a free carrier concentration of $8\times10^{12}$ cm$^{-3}$, doped with $1\times10^{11}$ cm$^{-3}$ Au. 2 cm$^2$ evaporated gold Schottky contacts and soldered In ohmic contacts were prepared. The wafer was mounted with 20 μm gold wires on a temperature controllable stage of a modified minority carrier lifetime measuring equipment, originally manufactured by Leo-Gikken Co. of Japan. Microwave generator 31 of Gunn diode type was used at a frequency of 9.6 GHz, the cavity 31 was open ended which functions as an antenna for the reflected microwave power, a temperature controllable wafer stage and a reflector were placed above it. The microwave detector 32 was a crystal detector and the microwave preamplifier 34 both had a frequency response from dc to 10 MHz. The sample was reverse biased to 20 V, and majority carrier filling pulses of 20 μs duration and 20 V amplitude were applied periodically.

Figure 5:
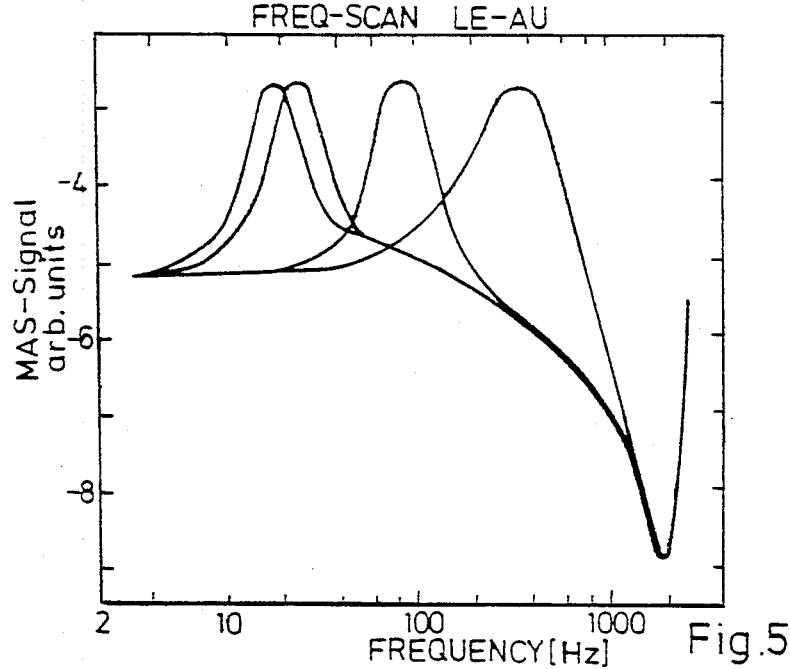
FIG. 5 shows the results of isothermal frequency scan measurements made at 4 different temperatures by the arrangement of FIG. 3.

The amplified microwave signal was fed into the lock-in amplifier 36 via the sample and hold circuit 35 which gated off the perturbations caused by the filling pulses. The whole system was controlled via an IBM PC controller i.e. computer 37. The lock-in amplifier 36 and the associated stages were part of a deep level spectrometer DLS-82E manufactured by Semitrap of Hungary. The sample was kept at different constant temperatures and frequency scan measurements (e.g. as described in "G. Ferenczi et. al, Phys. stat. sol. (a), 1986, 94, K119") were performed between 2 Hz and 2.5 kHz. The resulting spectra are illustrated in FIG. 5. The negative going peak at 2 kHz is an artifact of the measuring system (due to the capacitive coupling of the filling pulse via the stray capacitances).

The four positive going peaks measured at 241, 245, 255 and 267K. correspond to the emission of free carriers from the Au acceptor levels. The measured absorption signal originating from the change of the widths of the space charge layer due to the recharging of the Au acceptor level corresponds to a change of the microwave reflection coefficient caused by microwave absorption on $10^9$ electrons.

Figure 6:
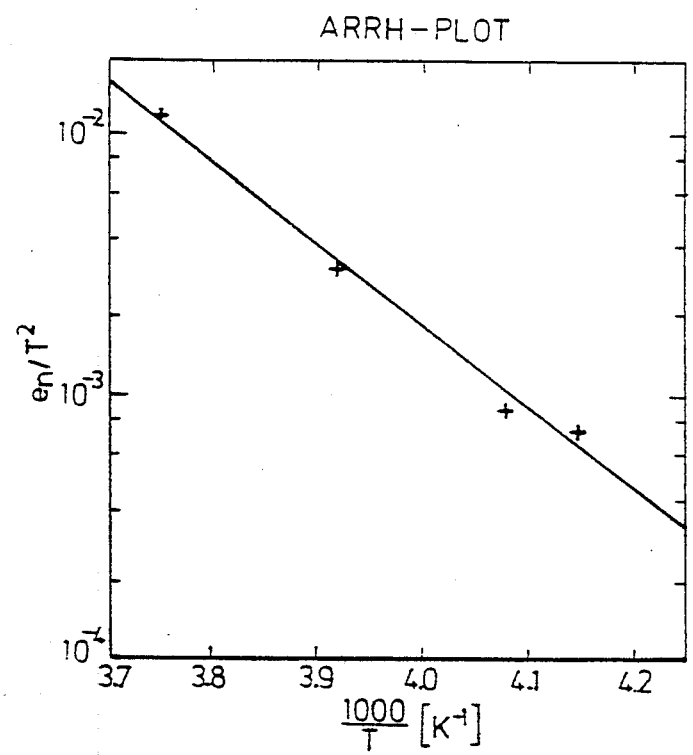
FIG. 6 shows the Arrhenius plot corresponding to the measurements of FIG. 5

It has to be noted that the microwave absorption signal amplitude remains constant independent of the temperature in contrast to capacitance DLTS measurements where the change in sample capacitance with temperature influences the signal amplitude. The Arrhenius plot corresponding to the results of FIG. 5 is shown in FIG. 6. The determined activation energy 0.56 eV is in agreement with the traditional space-charge spectroscopy data (D. V. Lang et al., Phys. Rev, 1980, B22, 3917).

Based on the above examples and the preceding considerations, it can be determined that compared with the transient capacitance DLTS measurements the substantially higher measuring frequency of the microwave signal (10 to 100 GHz compared to 1 MHz of the capacitance measuring signal) and the resulting shortening of the response time, which is at least 3 decimal orders of magnitude, have substantially enhanced the time range of the measurable transients. The pulses exciting the sample can be varied continuously practically between 0.01 Hz and 100 MHz i.e. the time coverage is about $10^{10}$ compared to the $10^5$ value in case of capacitance DLTS measurements. With such a high time coverage the frequency scan method is capable of examining activation energies between 0.1 and 0.7 eV at room temperature. The shortest applicable width of the exciting pulse is 100 ps due to the reasons discussed above and this short pulse provides also for the possibility that the capture cross section be measured up to $\sigma=10^{-12}$ cm² by means of changing the width of the exciting pulses. This upper limit is sufficient to the measurement of the practically highest deep level cross sections, therefore such measurements can also be carried out without changing the temperature of the sample.

By saving the necessity of changing the temperature, not only the time required for carrying out the measurements is reduced, but also the complexity of the equipment.

The smallest concentration detectable by the microwave absorption technique can be determined from the value of the smallest detectable change in absorption. If the detecting sensitivity of a Bruker type measuring system is considered to represent the highest available sensitivity, then according to the data given in the SRC Series Technical Manual of Bruker Co, the smallest detectable change in the electric field:

$$(\Delta E_r/R_o)_{min} = 10^{-9} \qquad (6)$$

wherein $\Delta E_r$ is the change of the electric field and
$E_o$ is the electric field in the cavity.

It can be calculated from the equation (6) that in case of a highly conductive and/or large sample $$(N_T/N_D)_{min} = 6 \cdot 10^{-7}, \qquad (7)$$

while in case of a less conductive and/or smaller sample (i.e. if the presence of the sample does not change the quality factor of the cavity to a significant extent):

$$(N_T)_{min} = 6 \cdot 10^7 \text{ cm}^{-3}. \qquad (8)$$

From this comparison it follows that even in the least favourable case microwave absorption measurements can provide the sensitivity comparable with that of capacitance DLTS technique (see equation (4) and in other cases the sensitivity is significantly higher and, what is even more significant, the threshold of detection is independent from the concentration of the free electrons.

Finally, it should be mentioned that by means of microwave absorption technique the changes in the concentration of the free charge carriers are measured, thus the measurement is not affected by the electrical parameters of the sample. In contrast to conventional capacitance or current DLTS measurements neither the series resistance nor the leakage current of the sample can limit the preformance of the measurements until space charge can be established in the sample.

Although a few number of methods of measuring microwave absorption have been shown, it must be appreciated that a number of other ways are also available for such measurements. Of such possibilities the application of a heterodyne detection sysem worth mentioning. In such a system a second microwave source is introduced whose frequency differs from that of the first one by a predetermined value. The detector can be replaced by a mixer which mixes the reflected microwave frequency $f_1$ with the frequency $f_2$ of the additional source. The output of the mixer contains both the sum and the difference of the two frequencies of which the component $f_1-f_2$ is selectively amplified by an intermediate frequency amplifier of suitable bandwidth. This component is also modulated by the periodic capture and emission processes. Such a principle is widely used in microwave signal reception and other fields of application. The invention cannot be limited to the way how the microwave absorption is sensed.

We claim:

1. A method for the examination of electrically active impurities in a semiconductor material with electrically active defects, comprising the steps of:
   (a) providing a junction capable of forming a space charge layer under reverse bias in a sample material, said junction being provided with a pair of contacts for biasing;
   (b) providing a space charge layer in said junction by reverse biasing said junction through biasing means coupled to said contacts;
   (c) filling the electrically active defects in said junction;
   (d) detecting a thermal emission process, said thermal emission process progressing towards a thermal equilibrium state that takes place following said filling step, wherein said sample material incorporating said junction is inserted in a microwave field from a microwave source at least during said detection step and in said detection step measuring the change of said microwave field strength that takes place due to changes in microwave absorption of said sample during said thermal emission process.

2. The method as claimed in claim 1, further comprising the step of periodically repeating said filling and detection steps.

3. The method as claimed in claim 2, wherein in association with the examination of a particular sample changing the frequency of said repetition to cover a range of at least 6 decimal orders of magnitude.

4. The method as claimed in claim 2, wherein in association with the examination of a particular sample changing the time of duration of said filling step and carrying out said examination even if said duration is shorter than 1 ns.

5. The method as claimed in claim 4, wherein said examination is carried out at a single temperature.

6. The method as claimed in claim 1, wherein said filling step is provided by the application of an electrical exciting pulse to said contacts, said pulse decreasing or eliminating said space charge region.

7. The method as claimed in claim 1, wherein said filling step is provided by light, by an electron beam or by means of an other radiation.

8. The method as claimed in claim 1, wherein said examinations are carried out at different constant temperatures.

9. The method as claimed in claim 1, comprising the step of continuously changing the temperature of said sample.

10. The method as claimed in claim 1, wherein said junction is provided by forming a Schottky barrier, a MOS capacitor or a p-n junction in said sample.

11. The method as claimed in claim 2, wherein said sample is exposed to said microwave field in a microwave resonator or in a microwave reflectometer.

12. The method as claimed in claim 11, further comprising the step of substantially eliminating said microwave field during said filling step.

13. Measuring arrangement for the examination of electrically active impurities of a semiconductor material, in which a sample of said semiconductor material comprises a junction, said sample being provided with a pair of electrical contacts, said arrangement comprising a biasing means coupled to said contacts for reverse biasing said junction to provide a space charge layer therein, a means for filling the electrically active defects in said layer during a predetermined period or periods, and transient detecting means for detecting transient changes in said junction after termination of said period or periods, characterized by comprising a microwave generator, a microwave means coupled to said generator and defining a microwave field, said sample being arranged in the microwave field of said microwave means with a contact coupled to earth, said transient detecting means being a microwave detector arranged to detect transient changes in microwave absorption due to said changes in said junction.

14. The measuring arrangement as claimed in claim 13, wherein said biasing and filling means comprises a pulse generator establishing periodic filling pulses and reverse biasing voltage during intervals of said pulses.

15. The measuring arrangement as claimed in claim 14, comprising a transmission line connecting said pulse generator to said sample.

16. The measuring arrangement as claimed in claim 13, wherein said microwave means is a cavity resonator and said sample is arranged in said resonator at the maximum of the electrical field.

17. The measuring arrangement as claimed in claim 13, wherein said microwave means is a microwave reflectometer.

18. The measuring apparatus as claimed in claim 13, further comprising a temperature controlling means capable of adjusting the temperature of said sample to predetermined values.

* * * * *